(12) United States Patent
Sathe et al.

(10) Patent No.: US 9,902,717 B2
(45) Date of Patent: Feb. 27, 2018

(54) PROCESS OF PREPARING POTASSIUM SALT OF AZILSARTAN MEDOXOMIL

(71) Applicant: Unichem Laboratories Limited, Mumbia, Maharashtra (IN)

(72) Inventors: Dhananjay G. Sathe, Maharashtra State (IN); Dnyaneshwar V. Gawas, Goa (IN); Sashikant D. Metkar, Maharashtra (IN)

(73) Assignee: UNICHEM LABORATORIES LIMITED (IN)

( * ) Notice: Subject to any disclaimer, the term of this patent is extended or adjusted under 35 U.S.C. 154(b) by 0 days.

(21) Appl. No.: 15/314,144

(22) PCT Filed: Mar. 21, 2016

(86) PCT No.: PCT/IB2016/051566
§ 371 (c)(1),
(2) Date: Nov. 28, 2016

(87) PCT Pub. No.: WO2016/151466
PCT Pub. Date: Sep. 29, 2016

(65) Prior Publication Data
US 2017/0197951 A1     Jul. 13, 2017

(30) Foreign Application Priority Data
Mar. 26, 2015 (IN) .......................... 1019/MUM/2015

(51) Int. Cl.
*C07D 413/14* (2006.01)

(52) U.S. Cl.
CPC ........ *C07D 413/14* (2013.01); *C07B 2200/13* (2013.01)

(58) Field of Classification Search
CPC .................................................... C07D 413/14
See application file for complete search history.

(56) References Cited

U.S. PATENT DOCUMENTS

| | | |
|---|---|---|
| 6,525,195 B1 | 2/2003 | Aguilar et al. |
| 2007/0265288 A1 | 11/2007 | Pathi et al. |
| 2014/0113942 A1* | 4/2014 | Dwivedi ............. C07D 413/10 514/364 |
| 2014/0364464 A1 | 12/2014 | Lei et al. |

FOREIGN PATENT DOCUMENTS

WO     2010111264 A2     9/2010

* cited by examiner

*Primary Examiner* — Matthew P Coughlin
(74) *Attorney, Agent, or Firm* — Hayes Soloway PC

(57) ABSTRACT

The present invention relates to a process for the preparation of Azilsartan Medoxomil Potassium. The invention further relates to novel highly crystalline polymorph of Azilsartan Medoxomil Potassium and composition comprising it. The invention provides thermostable highly crystalline polymorph of Azilsartan Medoxomil Potassium and process to produce a composition comprising the novel highly crystalline polymorph of Azilsartan Medoxomil Potassium.

16 Claims, 7 Drawing Sheets

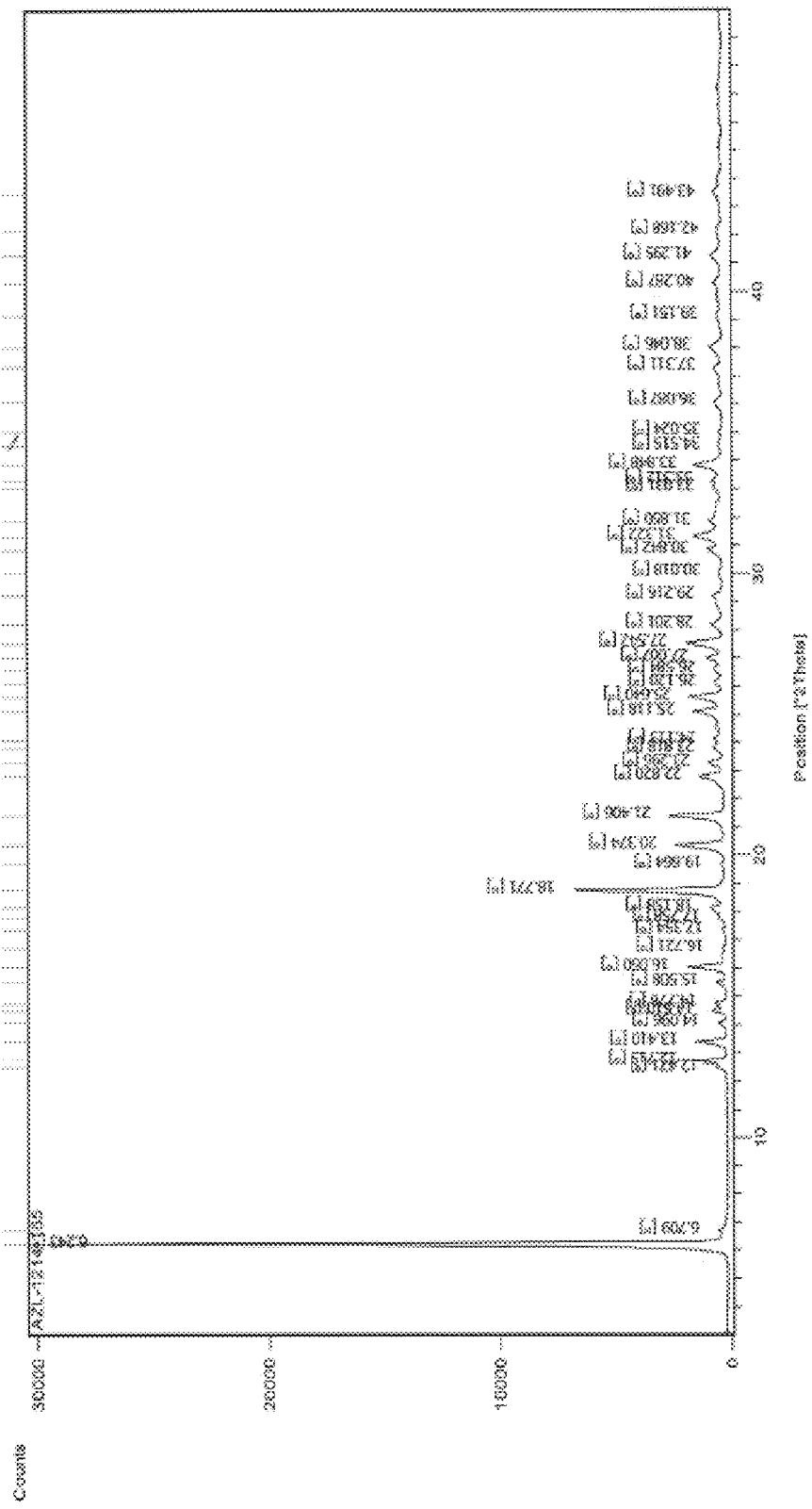
FIG. 1: X-ray powder diffraction pattern (XRPD) of the Azilsartan Medoxomil Potassium obtained according to example 1 (form-U).

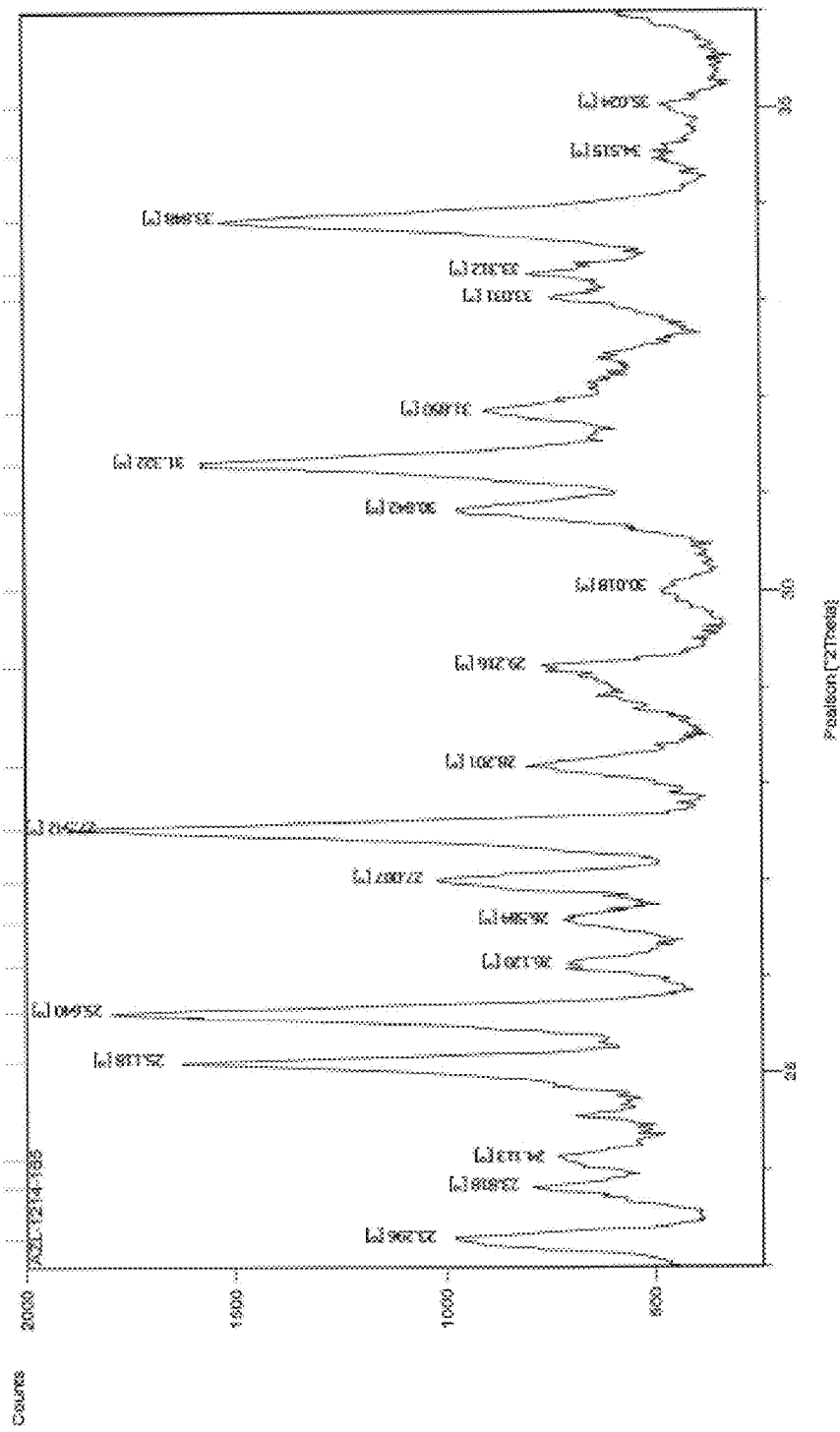
FIG. 1A: Expanded X-ray powder diffraction pattern (XRPD) of the Azilsartan Medoxomil Potassium obtained according to example 1 (form-U)

FIG. 1B: Table of values for the XRPD pattern depicted in FIG. 1

| Two theta values | d-spacing [A⁰] | Rel.Int. [%] |
|---|---|---|
| 6.2432 | 14.1572 | 100.00 |
| 6.7085 | 13.1762 | 1.41 |
| 12.4709 | 7.09790 | 1.48 |
| 12.7152 | 6.96112 | 4.48 |
| 13.4102 | 6.6027 | 4.28 |
| 14.0956 | 6.2832 | 1.12 |
| 14.5103 | 6.1045 | 2.07 |
| 14.7764 | 5.9952 | 1.52 |
| 15.5076 | 5.7141 | 1.24 |
| 16.0498 | 5.5223 | 5.30 |
| 16.7213 | 5.3020 | 0.42 |
| 17.3544 | 5.1100 | 0.52 |
| 17.7585 | 4.9946 | 0.92 |
| 18.1581 | 4.8856 | 1.90 |
| 18.7710 | 4.7274 | 21.35 |
| 19.6645 | 4.5146 | 0.55 |
| 20.3742 | 4.3589 | 6.92 |
| 21.4059 | 4.1511 | 7.74 |
| 22.8202 | 3.8969 | 3.25 |
| 23.2959 | 3.8184 | 2.11 |
| 23.8180 | 3.7359 | 1.43 |
| 24.1130 | 3.6908 | 1.23 |
| 25.1181 | 3.5454 | 4.17 |
| 25.6402 | 3.4744 | 4.63 |
| 26.1200 | 3.4116 | 1.12 |
| 26.5840 | 3.3531 | 1.14 |
| 27.0068 | 3.3016 | 1.12 |
| 27.5421 | 3.2386 | 5.07 |
| 28.2008 | 3.1644 | 1.39 |
| 29.2158 | 3.0568 | 1.32 |
| 30.0177 | 2.9769 | 0.37 |
| 30.8417 | 2.8992 | 2.01 |
| 31.3220 | 2.8559 | 3.98 |
| 31.8497 | 2.8097 | 1.74 |
| 33.0307 | 2.7119 | 1.25 |
| 33.3115 | 2.6897 | 1.36 |
| 33.8477 | 2.6483 | 3.75 |
| 34.5150 | 2.5986 | 0.41 |
| 35.0239 | 2.5620 | 0.35 |
| 36.0867 | 2.4890 | 0.87 |
| 37.3113 | 2.4100 | 1.01 |
| 38.0462 | 2.3652 | 1.62 |
| 39.1513 | 2.3009 | 0.58 |
| 40.2867 | 2.2386 | 1.10 |
| 41.2949 | 2.1863 | 1.53 |
| 42.1680 | 2.1430 | 0.57 |
| 43.4907 | 2.0791 | 1.06 |

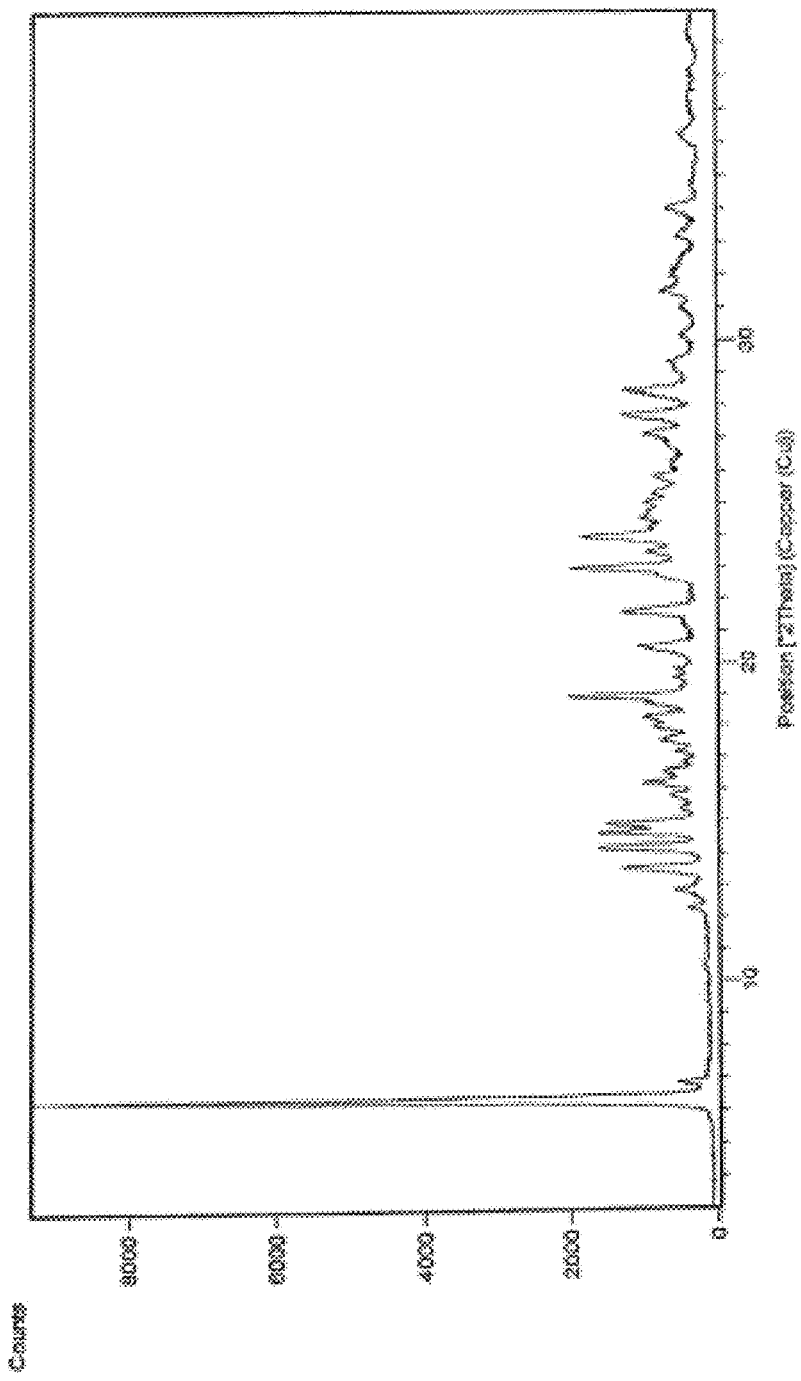
FIG. 2: The X-ray powder diffraction pattern (XRPD) of the potassium salt of Azilsartan Medoxomil obtained according to the comparative example

FIG. 2A: Table of values for the XRPD pattern depicted in FIGURE 2

| Two theta Values | d-spacing [Å] | Rel. Int [%] |
|---|---|---|
| 6.39 | 13.82 | 100 |
| 6.84 | 12.92 | 5.18 |
| 12.82 | 6.90 | 4.63 |
| 13.58 | 6.52 | 12.73 |
| 14.24 | 6.22 | 15.68 |
| 14.67 | 6.04 | 17.23 |
| 14.94 | 5.93 | 15.51 |
| 15.40 | 5.75 | 4.43 |
| 15.81 | 5.60 | 5.86 |
| 16.17 | 5.48 | 9.98 |
| 16.59 | 5.34 | 6.57 |
| 17.20 | 5.15 | 5.08 |
| 17.53 | 5.06 | 6.94 |
| 17.99 | 4.93 | 8.59 |
| 18.29 | 4.85 | 9.67 |
| 18.92 | 4.69 | 22.23 |
| 20.51 | 4.33 | 11.02 |
| 21.56 | 4.12 | 12.77 |
| 22.98 | 3.87 | 23.68 |
| 23.46 | 3.79 | 9.85 |
| 23.93 | 3.72 | 19.58 |
| 24.58 | 3.62 | 9.86 |
| 25.00 | 3.56 | 9.46 |
| 25.29 | 3.52 | 8.31 |
| 25.81 | 3.45 | 8.28 |
| 27.11 | 3.29 | 9.77 |
| 27.71 | 3.22 | 13.52 |
| 28.47 | 3.13 | 13.21 |
| 29.35 | 3.04 | 5.89 |
| 31.47 | 2.84 | 7.16 |
| 32.21 | 2.78 | 4.73 |
| 33.15 | 2.70 | 4.45 |
| 34.02 | 2.63 | 6.15 |
| 36.24 | 2.48 | 4.00 |

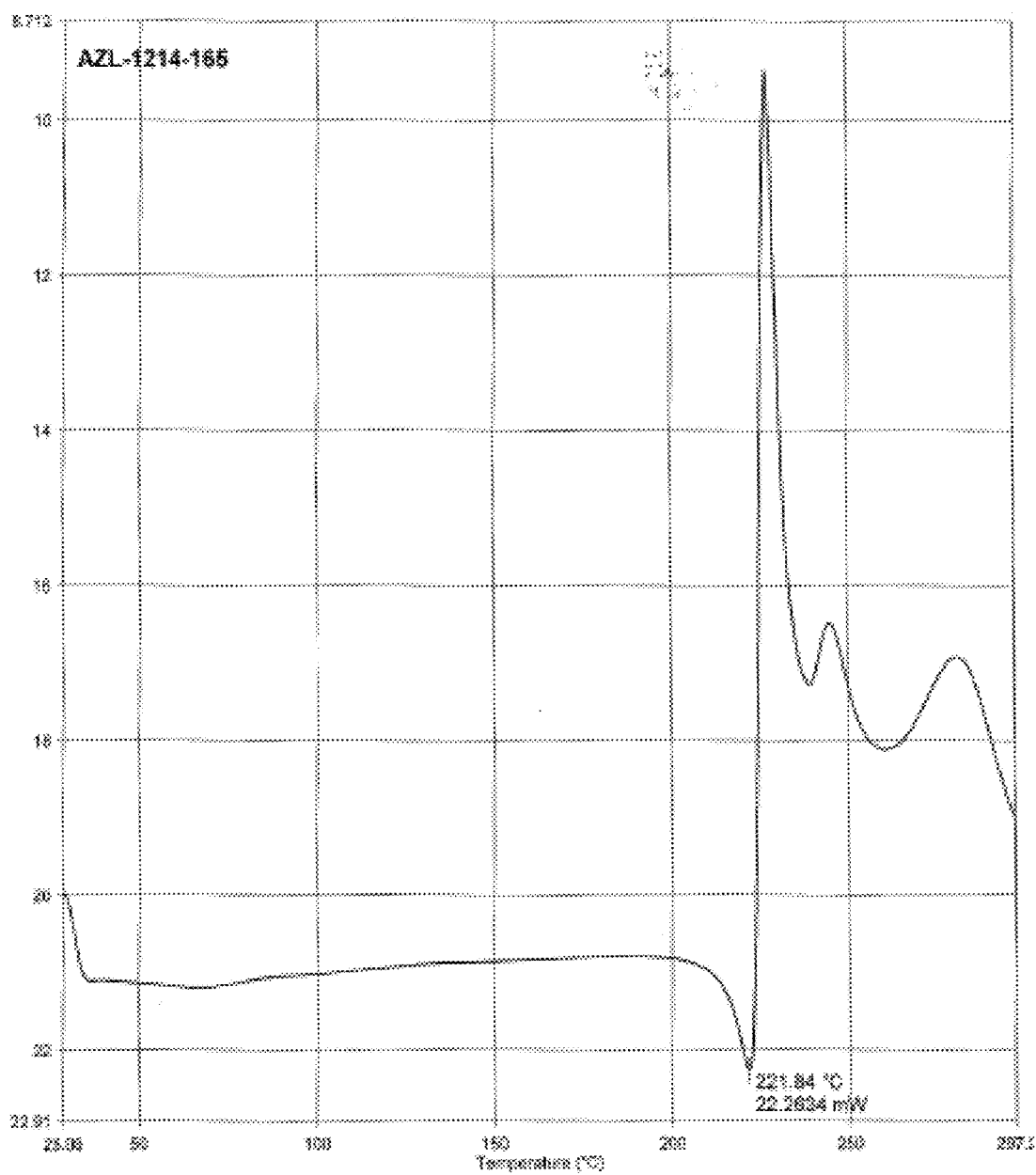
FIG. 3: DSC profile of Azilsartan Medoxomil Potassium in form-U

FIG. 4: Needle shaped crystal structure of Azilsartan Medoxomil Potassium in form-U
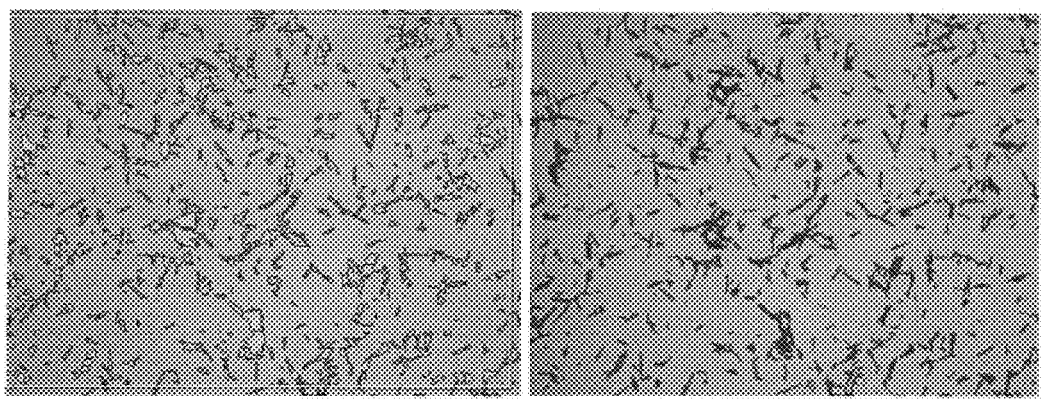
Result Summary
Fields 1
Field Area sq mm .034
Total Count 929
In Range Count 922
In Range % 99.2465

PROCESS OF PREPARING POTASSIUM SALT OF AZILSARTAN MEDOXOMIL

FIELD OF THE INVENTION

The present invention relates to a process for the preparation of Azilsartan medoxomil potassium and further relates to a highly crystalline form of Azilsartan medoxomil potassium.

BACKGROUND OF INVENTION

Azilsartan medoxomil potassium is chemically described as (5-methyl-2-oxo-1,3-dioxo-4-yl)methyl-2-ethoxy-1-1{[2'-(5-oxo-4,5-dihydro-1,2,4-oxadiazol-3-yl) biphenyl-4yl] methyl}-1H-benzimidazole-7-carboxylate monopotassium salt of Formula I.

Formula I

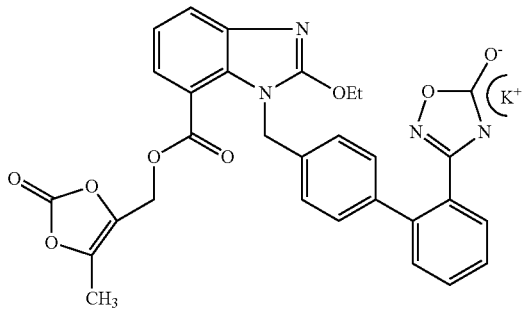

Azilsartan medoxomil potassium is a prodrug of Azilsartan of Formula II.

Formula II

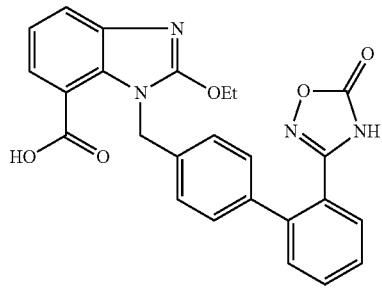

Azilsartan medoxomil potassium is an angiotensin II receptor blocker sold under the trade name EDARBI in USA and is indicated for the treatment of hypertension to lower blood pressure in the recommended dose of 40 mg taken once daily and escalation to 80 mg per day as necessary.

Azilsartan medoxomil potassium was described for the first time in U.S. Pat. No. 7,157,584 where its preparation and crystallization from acetone is presented, obtaining off-white crystal, having a melting point of 196° C.

U.S. Patent Application No. 20140113942 discloses process for preparation of Azilsartan medoxomil potassium Form I', the process comprising: (a) dissolving purified Azilsartan medoxomil methylene dichloride solvate in one or more of suitable organic solvent to obtain solution of solvate; (b) adding potassium source solution to the solution of solvate to obtain Azilsartan medoxomil potassium in reaction mixture; and (c) obtaining Azilsartan medoxomil potassium by removal of solvent from the reaction mixture.

International (PCT) publication WO 2013/042067 discloses process for preparation of Azilsartan medoxomil potassium Form I by treating Azilsartan medoxomil with potassium source in the presence of at least one C4-9 ketone solvent such as methyl ethyl ketone, methyl isobutyl ketone, methyl isopropyl ketone, ethyl isopropyl ketone, butanone or acetophenone.

PCT publication WO2013/104342 discloses crystalline form of Azilsartan medoxomil potassium, wherein the crystalline form is form A, form B, form C, form D, form E, form F, form G, form H, form I, form J, form K or form L and wherein the crystalline form of Azilsartan medoxomil potassium is substantially pure.

International (PCT) publication WO 2013/124748 discloses novel crystalline forms of Azilsartan medoxomil potassium and process for its preparation. WO 2013/124748 also discloses process for the preparation of amorphous Form VI of Azilsartan medoxomil potassium by the use of an organic solvent wherein the said organic solvent is C1-C5 alcohol or mixture thereof.

International (PCT) publication WO2014/048404 discloses process for the preparation of Azilsartan medoxomil potassium of formula I, in which first a solvate of Azilsartan medoxomil with a solvent selected from the group that consists of dimethyl acetamide or N-methyl pyrrolidone or their mixtures with other solvents is prepared, the resulting solvate is optionally re-crystallized, and, in the next step, converted, without desolvating, into the potassium salt using a potassium source.

Azilsartan medoxomil potassium exists in different crystalline forms, which have significant differences from each other in appearances, solubilities, melting points, dissolution rates, bioavailabilities, stability, efficacy and the like. These properties impact the stability of the substance and in turn impact the stability of the formulation in which it is incorporated. It is always desirable to use substance which is more thermostable as it ensures more stable pharmaceutical formulation. Therefore, there is a need for novel crystalline forms of Azilsartan medoxomil potassium which are thermostable and have higher melting point as compared to the melting points of existing crystalline forms.

OBJECT OF THE INVENTION

The main object of the invention is to provide a process to prepare Azilsartan Medoxomil Potassium.

Another object of the invention is to provide a novel highly crystalline polymorph of Azilsartan medoxomil potassium and the composition comprising the novel highly crystalline polymorph of Azilsartan medoxomil potassium.

Yet another object of the invention is to provide a thermostable highly crystalline polymorph of Azilsartan medoxomil potassium.

Yet another invention is to provide a more stable highly crystalline form of Azilsartan medoxomil potassium Yet another object of the invention is to provide the process to produce a composition comprising the novel polymorph of Azilsartan medoxomil potassium.

SUMMARY OF INVENTION

There is provided a process for the preparation of Azilsartan medoxomil potassium which comprises.

Dissolving Azilsartan medoxomil in a mixture of Chlorinated solvent and an Alcohol to obtain a clear solution and thus obtained clear solution was cooled to 0 to 5° C.

Dissolving organic or inorganic Potassium source in a mixture of Chlorinated solvent and an Alcohol to obtain a second solution and Adding second solution drop wise to a solution of Azilsartan medoxomil prepared in step A) at 0 to 5° C., to precipitate out Azilsartan medoxomil potassium.

Isolating Azilsartan medoxomil potassium.

There is provided a process for the preparation of Azilsartan medoxomil potassium which comprises.

Dissolving Azilsartan medoxomil in a mixture of Chlorinated solvent and an Alcohol at a temperature of 20° C. to 30° C. to obtain a clear solution and thus obtained clear solution was cooled to 0° C. to 5° C.

Dissolving organic or inorganic Potassium source in a mixture of Chlorinated solvent and an Alcohol at a temperature of 20° C. to 30° C. to obtain a second solution and Adding second solution drop wise to a solution of Azilsartan medoxomil prepared in step A) at 0° C. to 5° C., to precipitate out Azilsartan medoxomil potassium.

Isolating Azilsartan medoxomil potassium.

Steps A, B and C can be carried out over a wide temperature range. Depending upon the kind of chlorinated solvent and alcohol used to prepare the mixture, the temperature can be varied. Preferred temperature range is 0° C.-30° C.

According to another aspect of the present invention, there is provided a novel highly crystalline form of Azilsartan medoxomil potassium characterised by peaks in the powder x-ray diffraction spectrum having 2θ angle position at about 23.81, 26.12, 26.58, 31.84, 34.51 and 35.02±0.2θ as shown in FIG. 1 and/or by the DSC profile shown in FIG. 3. Microscopic studies reveal that novel crystalline form of Azilsartan medoxomil potassium according to present invention is needle shaped.

Another aspect of the invention is to provide a thermostable highly crystalline form of Azilsartan medoxomil potassium.

Another aspect of the invention is to provide a more stable highly crystalline form of Azilsartan medoxomil potassium.

Another object of the present invention is to provide pharmaceutical composition comprising therapeutically effective amount of novel highly crystalline Azilsartan medoxomil potassium together with one or more pharmaceutically acceptable excipients.

According to yet another aspect there us provided a process to produce the composition comprising the thermostable novel highly crystalline polymorph of Azilsartan Medoxomil Potassium. Accordingly the process comprises Granulating intragranular excipients with a binder solution having pH between 1.5 to 2.5

Drying the granules obtained in step A, preferably keeping LOD NMT 2.0%

Passing dried granules through suitable screen to obtain passed granules.

Blending sifted Azilsartan kamedoxomil and $1^{st}$ lot of Extra granular ingredients with passed granules obtained in step C, for suitable duration to obtain pre-compaction granules.

Compacting pre-compaction granules obtained in step D and passing the compacted mass through suitable screen to obtain post compaction granules.

Optionally blending post compaction granules obtained in step E with $2^{nd}$ lot Extra granular ingredients which were pre sifted through suitable screen for suitable time to obtain pre-lubricated granules.

Lubricating post compaction granules or pre-lubricated granules obtained in step E or F for suitable time with Sifted Magnesium stearate to obtain blend of lubricated granules.

Optionally compressing blend of lubricated granules obtained in step G with suitable tooling or filling the lubricated granules obtained in step G into capsules.

BRIEF DESCRIPTION OF THE ACCOMPANYING DRAWINGS

FIG. 1 depicts the x-ray powder diffraction pattern (XRPD) of the azilsartan medoxomil potassium obtained according to example 1 (form-U).

FIG. 1a depicts the expanded x-ray powder diffraction Pattern (XRPD) of the Azilsartan Medoxomil potassium showing characteristic peaks of Form U FIG. 1B provides the table of values for the XRPD pattern depicted in FIG. 1

FIG. 2 depicts the x-ray powder diffraction pattern (XRPD) of the azilsartan medoxomil potassium obtained according to Comparative example 1

FIG. 2A provides the table of values for the XRPD pattern depicted in FIG. 2.

FIG. 3 shows the DSC profile of azilsartan medoxomil potassium in form-U.

FIG. 4 depicts needle shaped crystals of azilsartan medoxomil potassium in form-U.

DETAILED DESCRIPTION OF THE INVENTION

There is provided a process for the preparation of Azilsartan medoxomil potassium which comprises.

Dissolving Azilsartan Medoxomil in a mixture of Chlorinated solvent and an Alcohol to obtain a clear solution and thus obtained clear solution was cooled to 0° C. to 5° C.

Dissolving organic or inorganic Potassium source in a mixture of Chlorinated solvent and an Alcohol to obtain a second solution and Adding second solution drop wise to a solution of Azilsartan medoxomil prepared in step A) at 0° C. to 5° C., to precipitate out Azilsartan medoxomil potassium.

Isolating Azilsartan medoxomil potassium.

Thus there is provided a process to produce potassium salt of Azilsartan medoxomil.

In one aspect of the present invention, there is provided a process for the preparation of azilsartan medoxomil potassium which comprises.

Dissolving Azilsartan medoxomil in a mixture of Chlorinated solvent and an Alcohol at a temperature of 20° C. to 30° C. to obtain a clear solution and thus obtained clear solution was cooled to 0° C. to 5° C.;

Dissolving organic or inorganic Potassium source in a mixture of Chlorinated solvent and an Alcohol at a temperature of 20° C. to 30° C. to obtain a second solution;

Adding second solution drop wise to a solution of Azilsartan medoxomil prepared in step A) at 0° C. to 5° C., to precipitate out Azilsartan medoxomil potassium; and Isolating Azilsartan medoxomil potassium.

Steps A, B and C can be carried out over a wide temperature range. Depending upon the kind of chlorinated solvent and alcohol used to prepare the mixture, the temperature can be varied. Preferred temperature range is 0° C.-30° C.

The terms 'Azilsartan Medoxomil Potassium', 'Potassium salt of Azilsartan Medoxomil' and 'Azilsartan Kamedoxomil' mean the same.

Prior art discloses use of chlorinated solvents or that of alcohols individually. Prior art does not teach use of mixture of these solvents to prepare highly crystalline Azilsartan Medoxomil Potassium. Surprisingly it is noticed that when either chlorinated solvent or an alcohol is used singularly, Azilsartan Medoxomil Potassium does not remain in solution for long time as compared to when the mixture of chlorinated solvent and an alcohol is used. Also the product of reaction is not highly crystalline.

Surprisingly it was noticed that when the mixture of Chlorinated solvent and an alcohol is used to dissolve, Azilsartan Medoxomil in Step A and Potassium source in Step B, Azilsartan Medoxomil remains in solution for longer period and subsequent mixing of two results into formation of new highly crystalline polymorph at later stage. Teachings of prior art when a singular solvent is used, does not motivate or direct the person skilled in the art to imagine that use of mixture of known solvents would result into highly crystalline form of Potassium salt of Azilsartan Medoxomil.

The solvent used in step A) and step B) is mixture of Chlorinated solvent and Alcohols selected from carbon tetrachloride, trichloroethylene (TCE), methylene dichloride (MDC), chloroform ($CHCl_3$) and an alcohol selected from C1 to C6 alcohols with straight or branched chains, wherein C1 alcohol contains single carbon e.g methanol, C2 alcohol contains 2 carbons e.g. ethanol and so on. Preferred alcohols are ethanol, n-propanol, and isopropyl alcohol.

Ratio of Chlorinated solvent to alcohol is in the range of 10:1 to 1:10. It was surprisingly noticed that the ratio adjusted in the range of 10:1 to 10:5 gives better results. Thus entire range of 10:1 to 1:10 ratios is within the ambit of the invention.

Precipitation in step C) is preferably carried out by stirring for two hours at a temperature of 20° C. to 30° C.

The azilsartan kamedoxomil in step D) is isolated by filtration, distillation or decantation of the solvent from the precipitate or any other method known in the art.

The potassium source used in step (B) may be organic or inorganic in nature. An inorganic potassium source may be potassium hydroxide, potassium carbonate or potassium bicarbonate. An organic potassium source may be potassium benzoate, potassium acetate or potassium 2-ethylhexanoate.

It was surprisingly noticed that when a mixture of solvent used in a particular ratio to contact Azilsartan medoxomil with a potassium source, the resultant potassium salt of Azilsartan medoxomil, exhibits novel XRPD pattern as depicted by FIG. 1. It was also surprisingly noticed that resultant potassium salt of Azilsartan medoxomil is thermostable as it has higher melting point as compared to the melting points of existing crystalline forms. Thermostable also refers to the stability of the crystalline form at higher temperature. Thermostable is also to be interpreted as form that does not undergo polymorphic change when incorporated into composition. Thus there is provided a thermostable polymorph U of Azilsartan Kamedoxomil.

The novel highly crystalline polymorphic form of Azilsartan medoxomil potassium prepared according to present invention is designated as form-U. It has needle shaped crystals as depicted in FIG. 4.

FIG. 1 depicts the XRPD (X-ray powder diffraction pattern) pattern exhibited by the novel highly crystalline polymorphic form form-U of Azilsartan medoxomil potassium prepared according to present invention.

The novel highly crystalline polymorphic Form U of azilsartan medoxomil potassium according to present invention is characterised by peaks in the powder x-ray diffraction spectrum having 2θ angle position at about 23.81, 26.12, 26.58, 31.84, 34.51 and 35.02±0.2θ. It is also characterized by peaks at 25.11, 25.64±0.2θ as shown in FIG. 1 and/or by the DSC profile shown in FIG. 3.

The novel highly crystalline polymorphic Form U of azilsartan medoxomil potassium according to present invention is further characterised by powder x-ray diffraction spectrum having 2θ angle position at about 6.24, 6.70, 12.47, 12.71, 13.41, 14.09, 14.51, 14.77, 15.50, 16.04, 16.72, 17.35, 17.75, 18.15, 18.77, 19.66, 20.37, 21.40, 22.82, 23.29, 23.81, 24.11, 26.12, 26.58, 27.00, 27.54, 28.02, 29.21, 30.01, 30.84, 31.32, 31.84, 33.03, 33.31, 33.84, 34.51, 35.02, 36.08, 37.31, 38.04, 39.15, 40.28, 41.29, 42.16, 43.49±0.2θ as in FIG. 1.

Azilsartan medoxomil potassium in highly crystalline form U is further characterised by the DSC profile shown in FIG. 3. The graph depicts an endothermal peak due to the melting of the product with onset at 200° C. and Peak at 221.84° C.

The novel highly crystalline polymorphic Form U of a potassium salt of Azilsartan medoxomil of the present invention may be used for developing pharmaceutical composition comprising potassium salt of Azilsartan medoxomil. The polymorphic Form U of a potassium salt of Azilsartan medoxomil of the present invention may also be used for the treatment of hypertension comprising a step of administering to a patient in need thereof a therapeutically effective amount.

Stability of novel highly crystalline polymorph U was studied at 5±3° C. and was found to be stable. There is provided a novel highly crystalline stable polymorph.

Novel polymorph, thermostable, stable highly crystalline, novel thermostable polymorph, highly crystalline polymorph, novel highly crystalline polymorph, polymorph U, novel highly crystalline polymorph U, Novel polymorph U terms are used interchangeably and mean highly crystalline polymorph.

A pharmaceutical composition comprising a novel crystalline Form U of a potassium salt of azilsartan medoxomil alternatively referred as Azilsartan kamedoxomil are prepared as described in examples.

The pharmaceutical composition comprises novel crystalline forms of azilsartan medoxomil potassium or Azilsartan kamedoxomil according to present invention, can be tablets, capsules, pills, powders or granules. The tablet composition and the process to formulate the same is explained in the examples. The novel crystalline Form U of a potassium salt of azilsartan medoxomil alternatively referred as Azilsartan kamedoxomil novel polymorph U is of versatile utility. It is process friendly and can be filled into capsules.

The composition comprising novel crystalline form of Azilsartan medoxomil potassium characterised by peaks in the powder x-ray diffraction spectrum having 2θ angle position at 23.81, 26.12, 26.58, 31.84, 34.51 and 35.02±0.2θ is conveniently prepared by following steps as listed hereafter.

Granulating intragranular excipients with a binder solution having pH between 1.5 to 2.5;

Drying the granules obtained in step A, preferably keeping LOD NMT 2.0%;

Passing dried granules through 30 # screen to obtain passed granules;

Blending sifted Azilsartan kamedoxomil and 1$^{st}$ lot of Extra granular ingredients with passed granules obtained in step C, for 15 min to obtain precompaction granules;

Compacting pre-compaction granules obtained in step D and passing the compacted mass through 30 # screen to obtain post compaction granules;

Optionally blending post compaction granules obtained in step E with 2$^{nd}$ lot Extra granular ingredients which were pre sifted through 30 # screen for 15 min. to obtain pre-lubricated granules;

Lubricating post compaction Granules obtained in step E or Pre-lubricated granules obtained in Step F for 3 min with 40 # screen Sifted Magnesium stearate to obtain blend of lubricated granules;

Compressing into tablets or filling the capsules with the blend of
a. lubricated granules obtained in step G.

Mixing times can be modulated to ensure the uniformity of contents primarily with respect to active ingredient that is Azilsartan kamedoxomil. These also depend upon the type of blender used and the mass to be mixed. The pharmaceutical compositions may include excipients or carriers, wherein the excipients or carriers comprise sodium citrate, calcium phosphate, fillers, binders, moisturizers, disintegrants, retarders, absorption enhancer, wetting agents, absorbents, lubricants and a combination thereof, wherein the fillers include starch, lactose, sucrose, glucose, mannitol, silicic acid and a combination thereof, wherein the binders include carboxymethylcellulose, alginates, gelatin, polyvinylpyrrolidone, sucrose, gum Arabic and a combination thereof, wherein the moisturizers include glycerol, wherein the disintegrants include agar-agar, calcium carbonate, potato starch or tapioca starch, alginic acid, certain silicates, and sodium carbonate, low substituted hydroxypropyl cellulose and a combination thereof; wherein the blockers solution include paraffin; wherein the absorption enhancer include quaternary ammonium compounds; wherein the wetting agents include cetyl alcohol, monostearic acid glyceride and a combination thereof; wherein the absorbents include kaolin, bentonite and a combination thereof; wherein the lubricants include talc, calcium stearate, magnesium stearate, solid polyethylene glycols, sodium lauryl sulfate and a combination thereof.

Thus there is provided a composition comprising the novel polymorph U f Azilsartan Kamedoxomil and process to produce a composition comprising the novel polymorph U of Azilsartan Kamedoxomil.

Azilsartan Medoxomil starting material is prepared by method known in literature.

XRPD of the samples was determined by using Panalytical®; Model: X'Pert PRO; in the range 3-40 degree 2θ, under tube voltage of 45 Kv and current of 40 mA. Copper radiation of wavelength 1.54 angstrom and Xceletor detector was used.

The terms novel form, novel polymorph and crystalline form are used interchangeably and mean the same i.e. novel polymorph.

The example is provided as one of the possible way to practice the invention and should not be considered as limitation of the scope of the invention.

COMPARATIVE EXAMPLE

Preparation of Azilsartan Kamedoxomil

Azilsartan medoxomil (3.0 g) was added to acetone (54 ml) at 20 to 30° C. and the reaction mixture was heated to 40° C. The reaction mixture was cooled to 0 to 5° C. A solution of potassium-2-ethyl hexanoate (0.96 g) in acetone (10.0 ml) was added dropwise to the reaction mixture at 0° C. to 5° C. The reaction mixture was stirred at 0° C. to 5° C. for 2 hours. The solid material precipitated out. The reaction mixture was further stirred for 4 hours. The reaction mixture was filtered at 0° C. to 5° C. and washed with acetone (6 ml). The reaction mixture was dried under vacuum at 40° C. to obtain the title compound having X-ray powder diffraction pattern (XRPD) as depicted in FIG. 2. Yield=2.2 gm, Melting point=196-199° C. decomposed. Purity=99.1

EXAMPLE

Example 1

Preparation of Potassium Salt of Azilsartan Medoxomil

Azilsartan medoxomil (3.0 g) was added to methylene dichloride (24 ml) and isopropyl alcohol (6 ml) at 20° C. to 30° C. and was stirred for 5 to 10 minutes to prepare a clear solution of Azilsartan Medoxomil. The clear solution was cooled to 0° C. to 5° C. Potassium-2-ethyl hexanoate (0.96 gm) was added to mixture of solvent of methylene chloride (7 ml) and isopropyl alcohol (2 ml) (total 9 ml) at 20° C. to 30° C. to prepare solution of potassium source. Potassium source solution was added drop wise to the clear solution of Azilsartan Medoxomil at 0 to 5° C. for 5 to 10 minutes with stirring. The temperature of the reaction mixture was raised to 20 to 30° C. and stirred for 2 hours. The solid obtained was filtered at 20 to 30° C. and washed with methylene chloride (6 ml) at 20 to 30° C. The solid was dried under vacuum at 40° C. to obtain the needle shaped crystals of title compound having X-ray powder diffraction pattern (XRPD) as depicted in FIG. 1. Yield=2.4 gm. M.P: 203-207° C. decomposed.

Example 2

Preparation of Azilsartan Medoxomil Potassium Using 10:1 Ratio MDC to IPA

Azilsartan medoxomil (10.0 g) was added to the mixture of methylene dichloride and isopropyl alcohol (100 ml; MDC:IPA=10:1) at 20° C. to 30° C. and was stirred for 5 to 10 minutes to prepare a clear solution of Azilsartan Medoxomil. The clear solution was cooled to 0° C. to 5° C. Potassium-2-ethyl hexanoate (3.2 gm) was added to mixture of solvent of methylene chloride and isopropyl alcohol (30 ml; MDC:IPA=10:1) at 20 to 30° C. to prepare solution of potassium source. Potassium source solution was added drop wise to the clear solution of Azilsartan Medoxomil at 0 to 5° C. for 5 to 10 minutes with stirring. The temperature of the reaction mixture was raised to 20 to 30° C. and stirred for 2 hours. The solid obtained was filtered at 20 to 30° C. and washed with methylene chloride (20 ml) at 20 to 30° C. The solid was dried under vacuum at 40° C. to obtain the needle shaped crystals of title compound.

Example 3

Preparation of Azilsartan Kamedoxomil Using MDC:IPA at 10:5

Azilsartan medoxomil (10.0 g) was added to methylene dichloride and isopropyl alcohol (100 ml; MDC:IPA=10:5)

at 20° C. to 30° C. and was stirred for 5 to 10 minutes to prepare a clear solution of Azilsartan Medoxomil. The clear solution was cooled to 0° C. to 5° C. Potassium-2-ethyl hexanoate (3.2 gm) was added to mixture of solvent of methylene chloride and isopropyl alcohol (30 ml; MDC: IPA=10:5) at 20 to 30° C. to prepare solution of potassium source. Potassium source solution was added drop wise to the clear solution of Azilsartan Medoxomil at 0 to 5° C. for 5 to 10 minutes with stirring. The temperature of the reaction mixture was raised to 20 to 30° C. and stirred for 2 hours. The solid obtained was filtered at 20 to 30° C. and washed with methylene chloride (20 ml) at 20 to 30° C. The solid was dried under vacuum at 40° C. to obtain the needle shaped crystals of title compound.

Example 4

Stability Study of Polymorph U of Azilsartan Kamedoxomil

The novel polymorph U was subjected to stability testing at 5±3° C. for 6 Months. There was no change in XRPD pattern. Thus it was confirmed that polymorph does not undergo polymorphic change. The results are listed in Table I below

TABLE I

| Test and Specification | Results | |
|---|---|---|
| | Initial | 6 M |
| 01) Description White to off-white coloured powder | White coloured powder | White coloured powder |
| 02) Identification By HPLC: The retention time of the major peak of the sample solution should correspond to that of the Azilsartan Kamedoxomil Standard preparation in assay by HPLC test. | Complies | Complies |
| 03) Loss on drying (at 60° C. under vacuum for 3 hrs) NMT 1.0% w/w | 0.44% w/w | 0.26% w/w |
| 04) Related substances Method 1: By HPLC (by Area %) | | |
| i) Azilsartan NMT 1.0% | 0.19% | 0.18% |
| ii) Azilsartan ester NMT 0.3% | 0.01% | 0.01% |
| iii) Impurity at RRT about 1.04 NMT 0.3% | 0.09% | 0.08% |
| iv) Any individual unspecified impurity NMT 0.2% | 0.03% | 0.03% |
| v) Total impurities NMT 2.5% | 0.56% | 0.43% |
| Method 2: By GCHS | | |
| i) Content of 2, 3 butanedione by GCHS: NMT 0.5% | 0.13% w/w | 0.13% w/w |
| 05) Assay by HPLC (On dried basis) NLT 97.5% w/w and NMT 102.0% w/w | 101.7 w/w | 100.3% w/w |

Example 5

Formulation Trial was Taken by Adjusting Binder Solution pH 2.5 with Sodium Hydroxide to Obtain a pH in Between 3-5 of Final Tablets Batch Size: 3000 Tablets

| S.N. | Ingredient | Percentage | Mg/Tablet |
|---|---|---|---|
| | Intragranular excipients | | |
| 1 | Mannitol (Pearlitol 25C) | 33.11 | 117.878 |
| 2 | MCC (Avicel PH 101) | 12.00 | 42.720 |
| | Binder Solution (5%) | 0.00 | |
| 3 | Fumaric acid | 1.12 | 4.000 |
| 4 | NaOH | 0.07 | 0.266 |
| 5 | Purified water | — | q.s. |
| 6 | HPC (Klucel LF) | 3.00 | 10.680 |
| | Extra granular after FBP for Roller compaction | | |
| 7 | Azilsartan kamedoxomil | 24.07 | 85.690 |
| 8 | Mannitol (Pearlitol SD 200) | 20.62 | 73.406 |
| 9 | Croscarmellose Sodium (Ac di sol) | 5.00 | 17.800 |
| | Lubrication | | |
| 10 | Magnesium Stearate | 1.00 | 3.560 |
| | Average weight of core tablet | | 356.00 |

Procedure:

1. Mannitol and MCC Sifted through 30 # screen and dry mixed in Fluidized Bed Equipment (FBE) for 10 min. LOD was 0.77% w/w;
2. Binder solution: NaOH and fumaric acid Dissolved in purified water (adjust pH 2.5 using 10% NaOH solution if required). Klucel LF was Dissolved with continuous stirring till clear solution obtained;
3. Step 1 blend was granulated in FBE with using step 2 binder solution and granules were dried till LOD NMT 1.0%;
4. Dried granules obtained in step 3 were passed through 30 # screen;
5. Azilsartan kamedoxomil and Extra granular ingredients Mannitol (Pearlitol SD 200), Croscarmellose sodium were sifted through 30 # screen and Blended with step 4 granules for 15 min;
6. Step 5 blend was compacted by using Roller Compactor; flakes were passed through 30 # screen to obtain granules;
7. Step 6 granules were lubricated for 3 min with 40 # screen Sifted Magnesium stearate;
8. Lubricated blend obtained in step 7 was compressed.

Example 6

Formulation by Replacing Sodium Hydroxide with Phosphoric Acid as Acidifying Agent to Adjust the pH Below 2.0 of Binder Solution to Obtain a Final Tablet's pH Between 3-5

Batch Size: 3000 Tablets

| S.N. | Ingredient | Percentage | mg/Tablet |
|---|---|---|---|
| | Intra granular for FBP | | |
| 1 | Mannitol (Pearlitol 25C) | 33.75 | 120.144 |
| 2 | MCC (Avicel PH 101) | 12.00 | 42.72 |
| | Binder Solution (5%) | | |
| 3 | Phosphoric acid | 0.56 | 2.00 |
| 4 | Purified water | — | q.s. |
| 5 | HPC (Klucel LF) | 3.00 | 10.68 |
| | Extra granular after FBP For Roller Compaction 1st lot | | |
| 6 | Azilsartan kamedoxomil | 24.07 | 85.69 |
| 7 | Croscarmellose Sodium (Ac-di-sol) | 2.00 | 7.12 |

-continued

| S.N. | Ingredient | Percentage | mg/Tablet |
|---|---|---|---|
| Extra granular after Roller Compaction 2$^{nd}$ lot | | | |
| 8 | Mannitol (Pearlitol SD 200) | 20.62 | 73.406 |
| 9 | Croscarmellose Sodium (Ac di sol) | 3.00 | 10.68 |
| Lubrication | | | |
| 10 | Magnesium Stearate | 1.00 | 3.56 |
| | Average weight of core tablet | | 356.00 |

Procedure:
1. Mannitol and MCC Sifted through 40 # screen and dry mixed in FBE for 10 min. LOD was 0.96%;
2. Binder solution: Phosphoric acid was Dissolved in purified water then Klucel LF was Dissolved with continuous stirring till clear solution obtained. pH of the binder solution was 1.7;
3. Step 1 blend was Granulated in FBE with using step 2 binder solution and granules were dried till LOD NMT 1.0% to obtain dried granules;
4. Dried granules obtained in step 3 were passed through 30 # screen;
5. Azilsartan kamedoxomil and Extra granular ingredient Croscarmellose sodium were sifted through 30 # screen and blended with step 4 granules for 15 min;
6. Step 5 blend was compacted by using Roller Compactor; flakes were passed through 30 # screen;
7. Extra granular ingredient after Roller compaction (Mannitol and Croscarmellose Sodium) were sifted through 30 # screen and blended with step 6 granules for 15 min;
8. Step 7 granules were lubricated for 3 min with 40 # screen Sifted Magnesium stearate to obtain blend of lubricated granules;
9. Blend of lubricated granules obtained in step 8 was compressed.

Example 7

Formulation Using Lubricated Blend of Example 3 for Filling in 'Size 0' Capsule

Batch Size: 3000 Capsules

| S. No. | Ingredient | Percentage | mg/Tablet |
|---|---|---|---|
| Intra granular for FBP | | | |
| 1 | Mannitol (Pearlitol 25C) | 33.75 | 120.144 |
| 2 | MCC (Avicel PH 101) | 12.00 | 42.72 |
| Binder Solution (5%) | | | |
| 3 | Phosphoric acid | 0.56 | 2.00 |
| 4 | Purified water | — | q.s. |
| 5 | HPC (Klucel LF) | 3.00 | 10.68 |
| Extra granular after FBP For Roller Compaction | | | |
| 6 | Azilsartan kamedoxomil | 24.07 | 85.69 |
| 7 | Croscarmellose Sodium (Ac-di-sol) | 2.00 | 7.12 |
| Extra granular after Roller Compaction | | | |
| 8 | Mannitol (Pearlitol SD 200) | 20.62 | 73.406 |
| 9 | Croscarmellose Sodium (Ac di sol) | 3.00 | 10.68 |
| Lubrication | | | |
| 10 | Magnesium Stearate | 1.00 | 3.56 |
| | Average weight of core tablet | | 356.00 |

Procedure:
1. Lubricated blend obtained in step 8 of Example 3 was filled in 'Size 0' Capsules;
2. All physical parameters were checked and were satisfactory.

We claim:
1. A process for the preparation of Azilsartan Medoxomil Potassium, which comprises:
   A) Dissolving Azilsartan Medoxomil in a mixture of a Chlorinated solvent and an Alcohol to obtain a clear first solution of Azilsartan Medoxomil;
   B) Dissolving an organic or inorganic Potassium source in a mixture of a Chlorinated solvent and an Alcohol to obtain a second solution;
   C) Adding the second solution obtained in step B), drop wise to the first solution of Azilsartan Medoxomil prepared in step A), to precipitate out Azilsartan Medoxomil potassium; and
   D) Isolating Azilsartan medoxomil potassium.
2. The process as claimed in claim 1, wherein the Chlorinated solvent in step A) and step B) is selected from carbon tetrachloride, trichloroethylene (TCE), methylene dichloride (MDC) and chloroform ($CHCl_3$).
3. The process as claimed in claim 1, wherein the Alcohol in step A) and step B) is selected from C1 to C6 alcohols with straight or branched chains.
4. The process as claimed in claim 1, wherein the mixture of the Chlorinated solvent and the Alcohol of step A) and step B) comprises the Chlorinated solvent and the Alcohol in the proportion of from 10:1 to 1:10.
5. The process as claimed in claim 1, wherein in step B) the organic potassium source is potassium benzoate, potassium acetate or potassium 2-ethylhexanoate.
6. The process as claimed in claim 1, wherein the inorganic potassium source of step B) is potassium hydroxide, potassium carbonate or potassium bicarbonate.
7. The process as claimed in claim 1, wherein the process of step A) and step B) is carried out at temperature from 20° C. to 30° C.
8. The process as claimed in claim 1, wherein the process of step C) is carried out at temperature from 0° C. to 5° C.
9. A process for the preparation of highly crystalline Form U of Azilsartan medoxomil potassium, wherein the process comprises steps of:
   A) Dissolving Azilsartan Medoxomil in a mixture of a Chlorinated solvent and an Alcohol to obtain a clear first solution of Azilsartan Medoxomil;
   B) Dissolving an organic or inorganic Potassium source in a mixture of a Chlorinated solvent and an Alcohol to obtain a second solution;
   C) Adding the second solution obtained in step B), drop wise to the first solution of Azilsartan Medoxomil prepared in step A), to precipitate out highly crystalline Form U of Azilsartan Medoxomil potassium; and
   D) Isolating the highly crystalline Form U of Azilsartan medoxomil potassium.
10. The process as claimed in claim 9, wherein the Chlorinated solvent in step A) and step B) is selected from carbon tetrachloride, trichloroethylene (TCE), methylene dichloride (MDC) and chloroform ($CHCl_3$).
11. The process as claimed in claim 9, wherein the Alcohol in step A) and step B) is selected from C1 to C6 alcohols with straight or branched chains.
12. The process as claimed in claim 9, wherein the mixture of the Chlorinated solvent and the Alcohol of step A) and step B) comprises Chlorinated solvent and an Alcohol in the proportion of from 10:1 to 1:10.

13. The process as claimed in claim 9, wherein the organic potassium source in step B) is potassium benzoate, potassium acetate or potassium 2-ethylhexanoate.

14. The process as claimed in claim 9, wherein the inorganic potassium source in step B) is potassium hydroxide, potassium carbonate or potassium bicarbonate.

15. The process as claimed in claim 9, wherein the process in step C) is carried at temperature from 0° C. to 5° C.

16. The process as claimed in claim 9, wherein the process in step A) and step B) is carried out at temperature from 20° C. to 30° C.

* * * * *